United States Patent [19]
Miyata et al.

[11] Patent Number: 5,711,754
[45] Date of Patent: *Jan. 27, 1998

[54] INTRA-AORTIC BALLOON CATHETER

[75] Inventors: Shinichi Miyata; Tetsuo Toyokawa; Kouichi Sakai, all of Yokohama; Masaru Miyahara, Tokyo; Takashi Tsuji, Fujisawa; Donald Robert Kirkpatrick, Tokyo, all of Japan

[73] Assignee: Nippon Zeon Co., Ltd., Tokyo, Japan

[*] Notice: The term of this patent shall not extend beyond the expiration date of Pat. No. 5,514,073.

[21] Appl. No.: 582,348

[22] Filed: Jan. 19, 1996

Related U.S. Application Data

[63] Continuation of Ser. No. 181,952, Jan. 18, 1994, Pat. No. 5,514,073, which is a continuation of Ser. No. 903,770, Jun. 25, 1992, abandoned.

[30] Foreign Application Priority Data

Jun. 27, 1991 [JP] Japan .................. 3-183386
Jun. 27, 1991 [JP] Japan .................. 3-183387

[51] Int. Cl.$^6$ ........................ A61N 1/362
[52] U.S. Cl. ............... 600/18; 604/96; 128/672
[58] Field of Search .............. 604/96–102, 283, 604/280, 43, 282; 606/192–195; 600/18; 128/672–675

[56] References Cited

U.S. PATENT DOCUMENTS

| | | | |
|---|---|---|---|
| 3,253,594 | 5/1966 | Matthews et al. | 604/96 |
| 4,261,339 | 4/1981 | Hanson et al. | |
| 4,311,133 | 1/1982 | Robinson | 606/194 |
| 4,327,709 | 5/1982 | Hanson et al. | |
| 4,467,790 | 8/1984 | Shiff | |
| 4,527,549 | 7/1985 | Gabbay | 606/192 |
| 4,546,759 | 10/1985 | Solar | 604/101 |
| 4,777,951 | 10/1988 | Cribier et al. | 604/96 |
| 4,785,795 | 11/1988 | Singh | 604/101 |
| 4,892,519 | 1/1990 | Songer et al. | 606/194 |
| 4,896,670 | 1/1990 | Crittenden | 606/194 |
| 4,909,787 | 3/1990 | Danforth | 604/22 |
| 4,917,666 | 4/1990 | Solar et al. | 606/194 |
| 4,952,357 | 8/1990 | Euteneuer | 604/96 |
| 4,958,634 | 9/1990 | Jang | 606/194 |
| 5,090,957 | 2/1992 | Moutafis et al. | 606/194 |
| 5,114,423 | 5/1992 | Kasprzyk et al. | 606/194 |
| 5,116,305 | 5/1992 | Milder et al. | 604/96 |
| 5,188,592 | 2/1993 | Hakki | 604/43 |
| 5,308,319 | 5/1994 | Ide et al. | 600/18 |

FOREIGN PATENT DOCUMENTS

| | | | |
|---|---|---|---|
| 62-114565 | 5/1987 | Japan. | |
| 63-206255 | 8/1988 | Japan. | |
| 1118329 | 10/1984 | U.S.S.R. | 604/99 |

Primary Examiner—Mark Bockelman
Attorney, Agent, or Firm—Birch, Stewart, Kolasch & Birch, LLP

[57] ABSTRACT

A balloon catheter has an inner tube communicating with a blood introduction port provided at a tip of the balloon portion. The inner tube is affixed to the inner wall of the catheter tube by adhesion, melt-bonding, or integral formation. The balloon catheter has a small channel resistance in the channel where the pressurized fluid which expands and contracts the balloon portion flows, even when the catheter tube has been bent, and enables expansion and contraction of the balloon portion with a good response. Another balloon catheter has the balloon portions at a range of the end sides of the balloon portions smaller in sectional area compared with the balloon portions at the tip sides. The catheter is able to effectively prevent side effects which occur only rarely but which are serious when they do occur. The catheter impairs as little as possible the effect of assisting the heart action inherent to the IABP method without special measurement of the diameter of the patient's blood vessels.

18 Claims, 4 Drawing Sheets

INTRA-AORTIC BALLOON CATHETER

This application is a continuation of application Ser. No. 08/181,952, filed on Jan. 18, 1994, now U.S. Pat. No. 5,514,073, which is a continuation of application Ser. No. 07/903,770, filed Jun. 25, 1992 now abandoned, the entire contents of which are hereby incorporated by reference.

BACKGROUND OF THE INVENTION

1. Field of the Invention

The present invention relates to a balloon catheter used for intra aortic balloon pumping which is a method of emergency treatment for patients suffering from low heart output due to acute cardiac insufficiency etc.

2. Description of the Related Art

Intra aortic balloon pumping (hereinafter abbreviated as "IABP") is a method of assisted circulation for treatment at times of reduced heart action, such as cardiac insufficiency, wherein a balloon catheter 2 comprised of a synthetic polymer material is inserted into the aorta as shown in FIG. 7 and the balloon portion 4 is expanded and contracted in accordance with the heart beat by introducing into and leading out from the balloon portion 4 a pressurized fluid from a catheter tube 6 by a pumping system 8 so as to assist the heart action.

As the balloon catheters usable for the IABP method, there are known the balloon catheters shown in Japanese Unexamined Published Patent Application (Kokai) No. 63-206255 and Japanese Unexamined Published Patent Application (Kokai) No. 62-114565. In such balloon catheters, for the balloon portions to expand and contract in accordance with the beat of the heart, it is necessary to detect the heart beat of a patient. As a means for detecting the heart beat of the patient, there is the means of attaching electrodes to the surface of the patient's body or in or outside of the heart and detecting the heart beat as an electrical signal.

As a means for judging if the method of assisted circulation of the IABP method is suitable or not from the blood pressure of the patient, there is the method of using a balloon catheter as shown in FIG. 8(a). In this method, an opening 5 is provided at the tip of the balloon portion 4 of the balloon catheter 2. An inner tube 10 communicating with this opening 5 is inserted inside the balloon portion 4 and the catheter tube 6 in the axial direction. By measuring the fluctuation in the blood pressure near the tip from the opening 5, it is possible to observe the effects of the method of assisted circulation of the IABP method.

However, there are the following problems in such a balloon catheter 2. As shown in FIG. 8(b), the catheter tube 6 of the balloon catheter 2 is inserted into the blood vessel by being snaked along the arterial blood vessels of the patient. Therefore, the inner tube 10 for measurement of the blood pressure ends up disposed irregularly snaked inside the catheter tube 6. As a result, when the pressurized fluid for expanding or contracting the balloon portion 4 flows through the gap between the outer wall of the inner tube 10 and the inner wall of the catheter tube 6, turbulence is caused, which increases the energy loss of the fluid and reduces the efficiency of the pump system 8 shown in FIG. 7 and also can cause deviation in the timing of the expansion and contraction. The period of the expansion and contraction of the balloon portion is a short period of about 0.6 second. The fluid reciprocates inside the catheter tube 6 during that short period, so the smaller the channel resistance the better.

Further, the conventional balloon catheters usable for the IABP method conform to the physical constitutions of specific people, they do not necessarily conform to the physical constitutions of other people and therefore, it has been pointed out, there is a danger of a detrimental effect on the blood flow in the celiac artery and the renal artery. To eliminate this problem, as disclosed in Japanese Unexamined Published Patent Application (Kokai) No. 63-206255, a balloon catheter has been developed which has dimensions and a shape conforming to the physical constitution of all people as well. Further, attempts are being made to adjust the maximum diameter and length of the balloon portion in accordance with the shape of the blood vessels of the individual patients subjected to the IABP method.

Such attempts are so as to prevent the side effect of damage to the patient's blood vessels due to the diameter of the balloon portion at the time of expansion becoming larger than the inner diameter of the patient's blood vessels, which infrequently occurs, and to prevent the side effect of embolism caused by damage to the balloon portion and leakage of drive gas from the balloon portion due to the outer circumference of the balloon portion sliding in contact against calcified deposits in the patient's blood vessels. It is desirable to adjust the maximum diameter and length of the balloon portion in accordance with the state of the patient's blood vessels, but the patient's blood vessels vary greatly in shape and making the volume of the balloon portion unnecessarily small to design to the safe side is not desirable considering the principle of the IABP method.

Further, measurement of the precise dimensions of a patient's blood vessels is fully possible technically, but when considering the burden on the patient and the trouble to the doctor, this is not necessarily a realistic means of solution.

The balloon portions of all IABP method balloon catheters currently on the market, including the balloon catheter disclosed in the above publication, are shaped with fixed sectional areas along the longitudinal direction or are shaped with the tip side and the end side substantially symmetric.

The present inventors have discovered a shape of a balloon catheter wherein it is possible to effectively prevent the side effect of damaging the patient's blood vessels by fundamentally changing the shape of the conventional balloon catheter and the side effect of embolism caused by damage to the balloon portion and leakage of the drive gas from the balloon portion due to the outer circumference of the balloon portion sliding in contact with calcified deposits in the patient's blood vessels and thus have completed the present invention.

SUMMARY OF THE INVENTION

The present invention has been made in consideration of these circumstances and has as its first object the provision of a balloon catheter which has a small channel resistance in the channel where the pressurized fluid which expands and contracts the balloon portion flows, even when the catheter tube has been bent, and enables expansion and contraction of the balloon portion with a good response.

Further, the present invention has as its second object the provision of a balloon catheter which is able to effectively prevent side effects which occur only rarely but which are serious when occurring and which impairs as little as possible the effect of assisting the heart action inherent to the IABP method without special measurement of the diameter of the patient's blood vessels.

To achieve the above-mentioned first object, the first balloon catheter of the present invention is comprised of a balloon catheter having a balloon portion which is inserted into an aorta and which expands and contracts so as to assist the heart action, a catheter tube which is connected so as to introduce into and lead out from the balloon portion a pressurized fluid, and an inner tube which communicates to a blood introduction port provided at a tip of said balloon portion and extends through the balloon portion and catheter tube in the axial direction, wherein the inner tube is affixed to the inside wall of said catheter tube. The inner tube may be formed integrally with the inner wall of the catheter tube.

In the first balloon catheter of the present invention, the inner tube communicating with the blood introduction port provided at the tip of the balloon portion is affixed to the inner wall of the catheter tube by adhesion, melt-bonding, integral formation, or other means, so even if the catheter tube is snaked along the arterial blood vessel, the inner tube remains affixed at a predetermined position of the inner wall of the catheter tube. Therefore, it is possible to effectively prevent the generation of turbulence and an increase in the channel resistance caused by the snaking of the inner tube in the catheter tube as in the prior art. Further, in the balloon catheter of the present invention, there is little energy loss of the pressurized fluid for the expansion and contraction of the balloon portion. As a result, the efficiency of the pumping system for driving the pressurized fluid is improved and also the pressurized fluid is introduced into or led out from the balloon portion quicker due to the drive of the pumping system, so the balloon portion expands and contracts with good timing and the effect of assisting the heart action is improved.

To achieve the above-mentioned second object, the second balloon catheter of the present invention is comprised so that the sectional areas of the tip side and the end side of the balloon portion differ and the sectional area gradually becomes smaller toward the end side from any position from the tip of the balloon portion toward the end side.

Further, the second balloon catheter of the present invention may be comprised so that the sectional areas of the tip side and the end side of the balloon portion differ, a level difference portion is provided at any position from a position about ¼ of the total length of the balloon portion from the tip of the same toward the end side, and the sectional area of the end side becomes smaller compared with the tip side.

In the second balloon catheter of the present invention, the balloon portion in a range from a predetermined position of the balloon portion to the end side becomes smaller in sectional area compared with the balloon portion at the tip side. Investigating the examples of damage to balloon portions with asymmetric tips and ends used for conventional balloon catheters, the damage most often occurs at the end sides of the balloon portions. The present inventors have guessed that the reason for this is that the aorta becomes narrower in the direction away from the heart. If, while the aorta becomes narrower in the direction away from the heart, the sectional shape of the balloon portion is symmetric between the tip side and the end side, the contact pressure between the outer circumference of the balloon portion and the inner walls of the blood vessels may be considered to become higher at the end side.

The balloon portion in the balloon catheter of the present invention becomes narrower from the tip to the end side over the entire length of the balloon portion, so the probability of damage at this portion becomes extremely small. Further, simultaneously, there is less fear of damaging the patient's blood vessels.

Further, since the region where the sectional area of the balloon portion becomes smaller is made the minimum necessary, there is no reduction in the effect of assisting the heart action of the IABP method.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Other objects and features of the present invention will be described in detail with reference to accompanying drawings in which, which are given by way of illustration only, and thus are not limitative of the present invention.

BRIEF DESCRIPTION OF THE PREFERRED EMBODIMENTS

Below, an explanation will be made of embodiments of the present invention with reference to the drawings.

Figure 1:
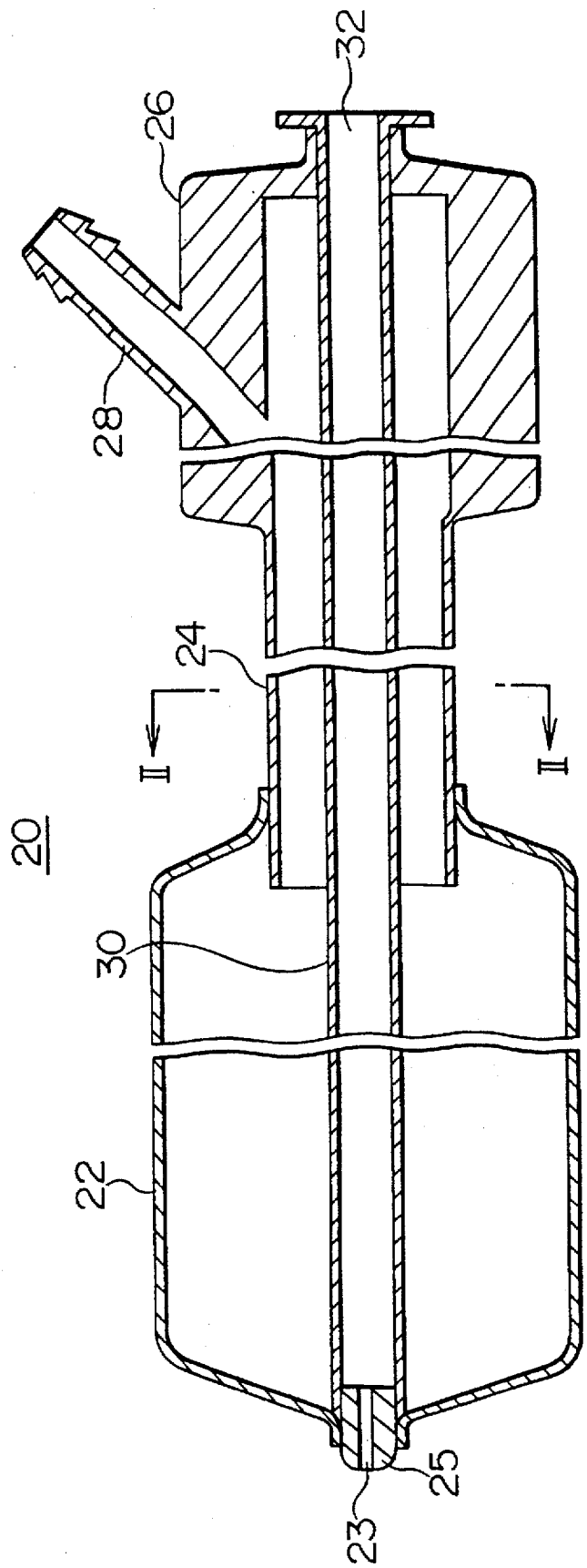
FIG. 1 is a schematic sectional view of a balloon catheter of an embodiment of the present invention.

As shown in FIG. 1, the balloon catheter 20 according to an embodiment of the present invention has a balloon portion 22 which expands and contracts in accordance with the beat of the heart. The balloon portion 22 is comprised of a thin film of a thickness of about 0.1 mm. The material of the thin film is not particularly limited, but it is preferably a material superior in resistance to flexural fatigue, for example, is comprised of polyurethane etc. At the tip of the balloon portion 22 comprised of the thin film, a cap 25 with a blood introduction port 23 formed therein is attached by heat-bonding, adhesion, or other means. At this cap 25, the tip of the inner tube 30 is attached by heat-bonding, adhesion, or other means. The inner tube 30 extends through the balloon portion 22 and the catheter tube 24 in the axial direction and communicates with a blood pressure measurement opening 32 mentioned later. The inside portion of the inner tube is not communication with the inside of the balloon portion 22.

The inner tube 30 positioned in the balloon portion 22 also acts as a support for when the contracted balloon portion 22 is wound up so that the balloon portion 22 may be conveniently inserted into the artery when the balloon catheter 20 is inserted into the artery.

The tip of the catheter tube 24 is connected at the end of the balloon portion 22. The fluid pressure is introduced into or led out from the balloon portion 22 through the catheter tube 24 so that the balloon portion 22 may expand or contract. The connection between the balloon portion 22 and the catheter tube 24 is made by heat-bonding, adhesion by a UV curing resin or other adhesive, etc.

A branch portion 26 disposed outside of the patient's body is connected to the end of the catheter tube 24. The branch portion 26 may be formed separately from the catheter tube 24 and be affixed by heat-bonding, adhesion, or other means and also may be formed integrally with the catheter tube 24. The branch portion 26 has formed in it a pressurized fluid introduction and discharge port 28 for introducing the pressurized fluid into the catheter tube 24 and the balloon portion 22 and discharging it from the same and a blood pressure measurement opening 30 communicating with the inside of the inner tube 32.

Figure 7:
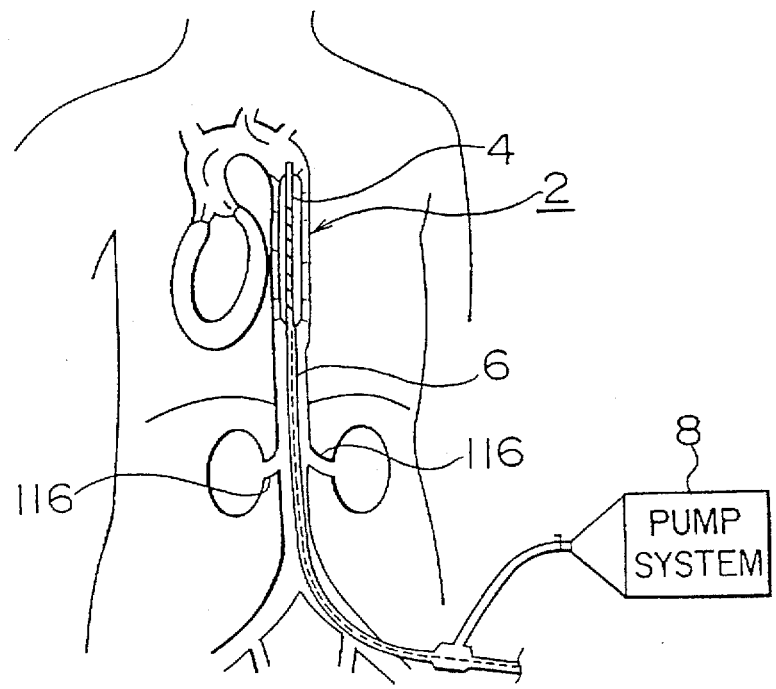
FIG. 7 is a schematic sectional view of the case of the balloon catheter attached inside an artery of a patient.
Figure 8A:
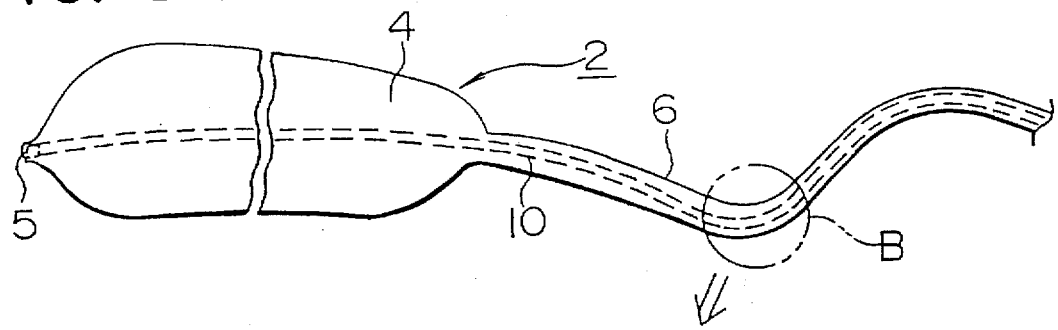
FIG. 8 shows a balloon catheter of the prior art, wherein (A) is a perspective view and (B) is a sectional view of key portions.
Figure 8B:
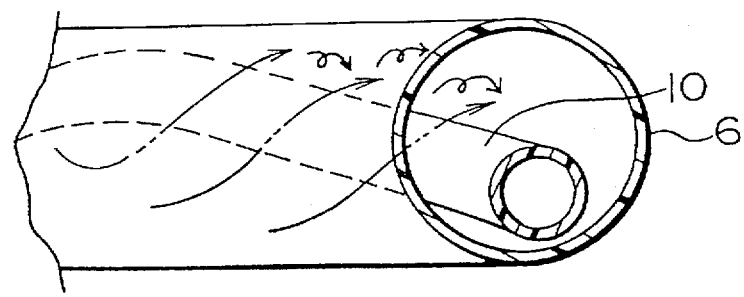

The pressurized fluid introduction and discharge port 28 is connected to the pump system 8 shown in FIG. 7. The fluid pressure is introduced into or led out from the balloon portion 22 by the pump system 8. As the fluid which is introduced, while not particularly limited, use is made of helium gas etc., with has a small viscosity, so that the balloon portion can expand and contract quickly in accordance with the drive of the pump system 8. The pump system 8 is not particularly limited. And it may be made of any known apparatus.

A blood extraction port 32 is connected, for example, to a blood pressure measurement apparatus, so as to enable measurement of the fluctuation in the blood pressure in the artery near the tip from the blood pressure measurement opening 23. Based on the fluctuations of the blood pressure measured by the blood pressure measurement apparatus, the heart beat is detected. The pump system 8 shown in FIG. 7 is controlled in accordance with the heart beat so as to cause the balloon portion 22 to expand or contract.

Figure 2:
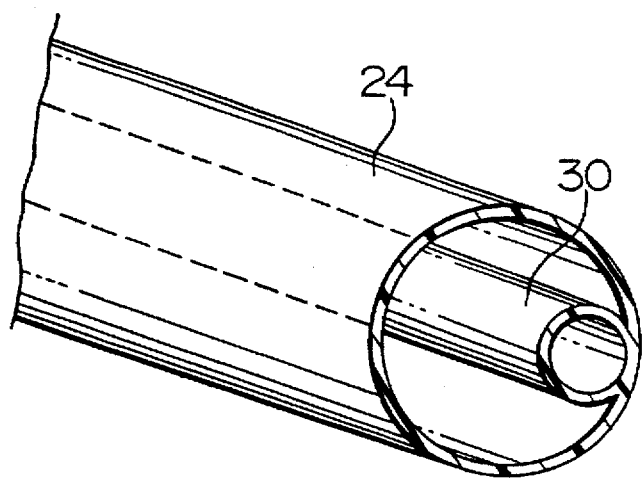
FIG. 2 is a sectional view along the line II—II in FIG. 1.
Figure 3A:
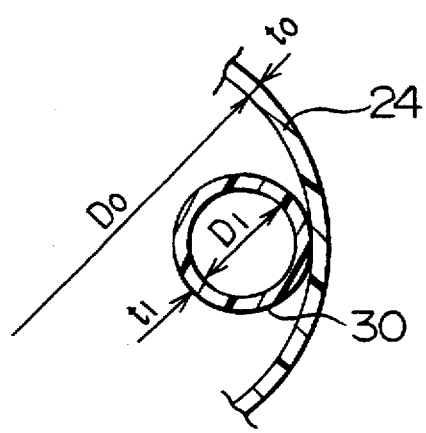
FIGS. 3(A) and 3(B) are partial sectional views of key portions of the catheter tube of the balloon catheter of the embodiment of the present invention.
Figure 3B:
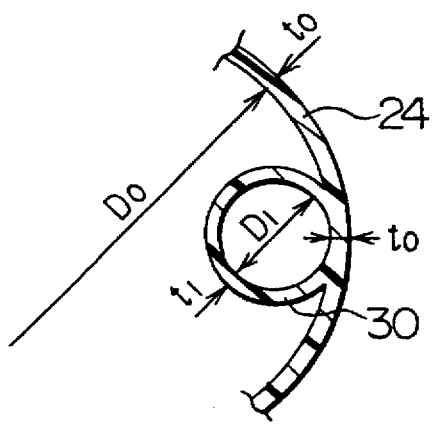

In this embodiment, as shown in FIG. 2, the inner tube 30 extending in the catheter tube 24 in the axial direction thereof is affixed to the inner wall of the catheter tube 24 by adhesion, heat-bonding, integral formation, or other means. An example of the inner tube 30 affixed to the inner wall of the catheter tube 24 by heat-bonding, adhesion, or other means is shown in FIG. 3(A), while an example of it being affixed by being formed integrally with it is shown in FIG. 3(B). The circumferential position of affixment between the inner tube 30 and the catheter tube 24 is preferably constant along the axial direction of the catheter tube 24 so that the inner tube 30 extends in a straight manner. But sometimes the circumferential position of affixment may be irregular whereby the inner tube 30 draws a gentle spiral shape along the inner wall of the catheter tube 24.

When adhering or heat-bonding the inner tube 30 to the inner wall of the catheter tube 24 as shown in FIG. 3(A), the catheter tube 24 and the inner tube 30 may be of the same material, but may also be of different materials. The material constituting the catheter tube 24 and the inner tube 30 is not particularly limited. Use is made of polyurethane, polyvinyl chloride, polyethylene, nylon, etc. These tubes 24 and 30 are formed, for example, by extrusion and are adhered or heat-bonded in a later step. During the adhesion, use may be made of, for example, a UV curing resin.

The inner diameter $D_0$ and the thickness $t_0$ of the catheter tube 24 are not particularly limited, but the inner diameter $D_0$ is preferably 1.5 to 4.0 mm and the thickness $t_0$ is preferably 0.05 to 0.4 mm. Further, the inner diameter $D_1$ and the thickness $t_1$ of the inner tube 30 are not particularly limited, but the inner diameter $D_1$ is preferably 0.1 to 1.0 mm and the thickness $t_1$ is preferably 0.05 to 0.4 mm.

As shown in FIG. 3(B), when forming the inner tube 30 integrally with the inner wall of the catheter tube 24, only naturally the catheter tube 24 and the inner tube 30 are comprised of the same material. As the means for forming them integrally, for example, use may be made of the method for extrusion of irregularly shaped tubes. If the inner tube 30 and the catheter tube 24 are affixed by such integral forming, the thickness of the joint portion becomes the thickness $t_0$ of the catheter tube 24 and it is possible to make the thickness smaller than the embodiment shown in FIG. 3(A), so the channel sectional area of the pressurized fluid in the catheter tube 24 may be increased by about 4 or 5 percent, which is convenient.

By adopting such a construction, the inner tube 30 can be affixed to a predetermined position of the inner wall of the catheter tube 24 even if the catheter tube 24 is snaked along the arterial blood vessel. Therefore, it is possible to effectively prevent the generation of turbulence and an increase in the channel resistance caused by the snaking of the inner tube in the catheter tube. Further, in the balloon catheter of the present invention, there is little energy loss of the pressurized fluid for expanding and contracting the balloon portion.

Next, a detailed explanation of another embodiment of the present invention will be given.

Figure 4:
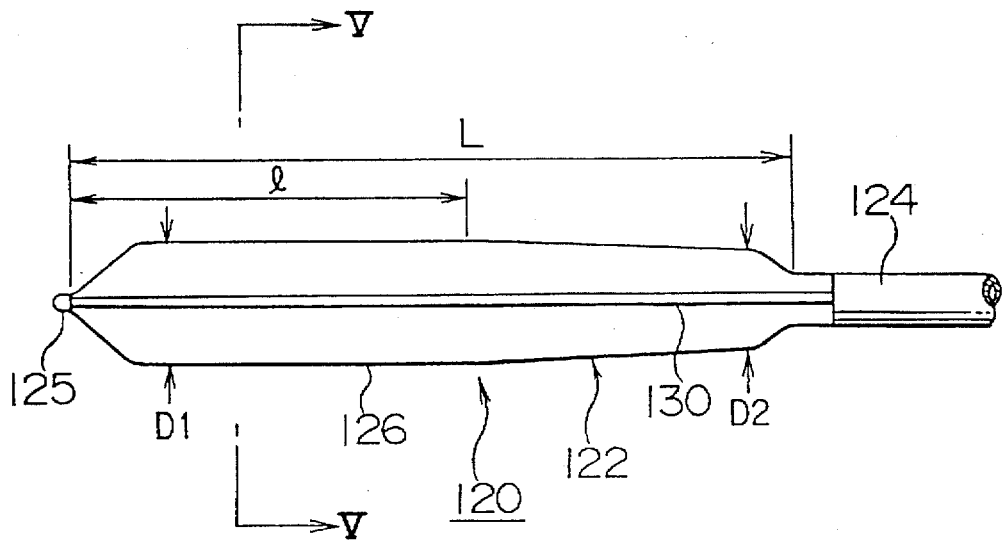
FIG. 4 is a sectional view of key parts of the balloon portion of a balloon catheter of the other embodiment of the present invention.
Figure 5A:
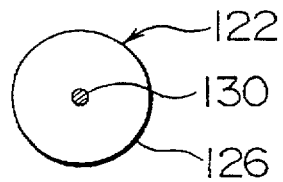
FIG. 5 is a sectional view along the line V—V in FIG. 4, wherein (A) shows the state of the balloon portion when expanded and (B) shows the state when contracted.

As shown in FIG. 4, the balloon catheter 120 according to another embodiment of the present invention has a balloon portion 122 which expands and contracts in accordance with the beat of the heart. The balloon portion 122 has a thin film 126 of a thickness of about 0.1 mm. The material of the thin film 126 is not particularly limited, but it is preferably a material superior in resistance to bending fatigue, for example, is comprised of polyurethane etc. The end of the balloon portion 122 comprised of the thin film 126 is penetrated by a catheter tube 124. Fluid pressure is introduced into or lead out from the balloon portion 122 through this catheter tube 124, whereby the balloon portion expands in circular sectional shape as shown in FIG. 5(A) or contracts as shown in (B) of the figure.

The catheter tube 124 is connected to a pump system 8 disposed outside of the body as shown in FIG. 7. Fluid pressure is introduced into or led out from the balloon portion 122 by the pump system 8. The fluid which is introduced is not particularly limited, but use is made of helium gas etc. having a small viscosity so that the balloon portion will expand or contract quickly in accordance with the drive of the pump system 8. Further, the pump system 8 is not particularly limited and a known apparatus may be used.

Figure 5B:
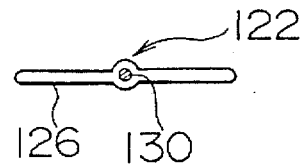

As shown in FIGS. 4 and 5, inside the balloon portion 122, there is attached in the axial direction a support member 130 mounted at its tip to a tip cap 125 of the balloon portion. This support member 130 is comprised of a wire material etc. having elasticity. When inserting the balloon catheter 120 inside the artery, the thin film 126 of the contracted balloon portion 122 is wound around so that the balloon portion 122 can be conveniently inserted into the artery.

Note that in the present embodiment, the material and the structure of the support member 130 are not particularly limited and various modifications are possible. For example, the member may be constructed so as to form a channel for measurement of the blood pressure inside the support member 130 along the axial direction similar to the inner tube 30 shown in FIGS. 1-3. In this case, it is necessary to provide in the tip cap 125 a blood introduction port for introducing the blood from there to the channel inside of the support member. The support member 130 may be affixed to the inside wall of the catheter tube 124 in the same manner as the embodiments shown in FIGS. 1–3.

In the embodiment, as shown in FIG. 4, the balloon portion 122 is shaped with the tip side and the end side being asymmetrical. It tapers toward the end side of the balloon portion 122 so that the sectional area gradually becomes smaller from a predetermined position 1 of the tip of the balloon portion 122 toward the end side. The predetermined position 1 from the tip, when the total length of the balloon portion is L, is sufficient if more than 0 (including 0) and may be changed in various ways such as to near ¼ L, near ½ L, near ¾ L, near 8/10 L, or near 9/10 L. However, the predetermined position 1 is desirably not more than 9/10 L, preferably not more than 8/10 L, more preferably not more than ¾ L.

In the present embodiment, the enlarged diameter D1 of the balloon portion at the position of the range of 1 from the tip in the balloon portion 122 is not particularly limited, but is preferably 12 to 20 mm, more preferably 13 to 16 mm. Further, the enlarged diameter D2 of the portion positioned most toward the end side of the balloon portion 122 is not particularly limited, but is preferably 4 to 16 mm, particularly preferably 6 to 10 mm. Also, the total length L of the balloon portion 122 is not particularly limited so long as the end of the balloon portion 122 is a length of a degree where the branch artery 116 to the kidney shown in FIG. 7 is not blocked, but is preferably 100 to 450 mm, more preferably 200 to 320 mm. Further, as the balloon catheter, it is preferable to prepare one which has a balloon portion 122 having several internal volumes such as 20 ml, 25 ml, 30 ml, 35 ml, and 40 ml in accordance with the physical constitution of the patient.

Note that the inner diameter of the thoracic aorta of the average adult Japanese male is 13.1 mm and the inner diameter of the abdominal aorta is 9.6 mm. For adult females, the values are 12.3 mm and 8.6 mm, respectively.

By adopting the above-mentioned constitution, it is possible to prevent extremely well damage to the balloon portion 120 and possible to improve the durability of the balloon catheter and, further, it is possible to effectively prevent damage to the patient's blood vessels. Further, despite this, the volume of the balloon portion 122 does not become much smaller than that in the prior art and there is no reduction of the effect of assisting the heart action of the balloon catheter 120.

Figure 6:
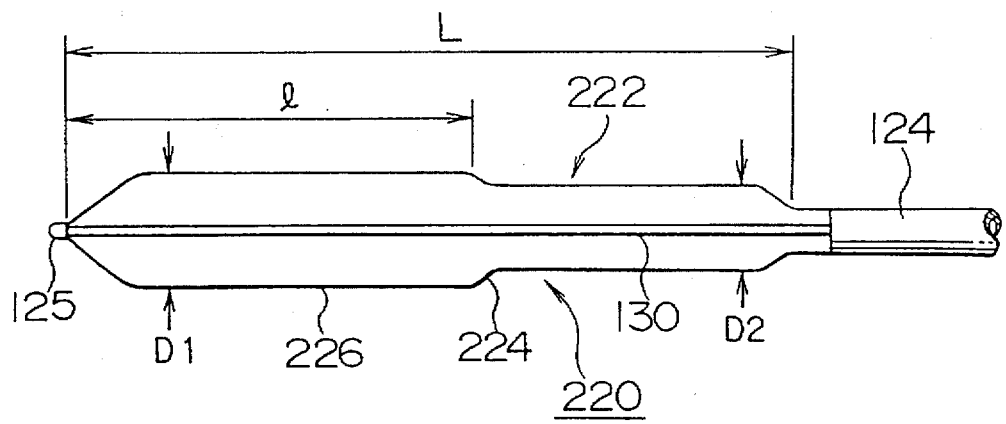
FIG. 6 is a sectional view of key parts of a balloon portion of a balloon catheter according to another embodiment of the present invention.

FIG. 6 shows a balloon catheter 220 according to further another embodiment of the present invention.

As shown in the figure, the balloon catheter 220 has a balloon portion 222 of a shape asymmetric between the tip side and the end side. The balloon portion 222 in this embodiment is comprised of the same thin film 226 as in the aforementioned embodiment (shown as "126"). Preferably a level difference portion 224 is provided at one position from the tip of the balloon portion 222 so that the sectional area of the end side becomes smaller than the tip side. The taper length of the level difference portion 224 is not particularly limited. The distance 1 from the tip of the balloon portion 222 may be any position in so far as it is more than ¼ of the total length L. Note that in this embodiment, only one level difference portion is provided, but it is also possible to provide a plurality in the area toward the end.

The outer diameter D1 of the tip side of the balloon portion 222 is the same as the outer diameter D1 of the tip side of the balloon portion according to the embodiment shown in FIG. 4. Further, the outer diameter D2 of the end side of the balloon portion 222 is the same as the outer diameter D2 of the end side of the balloon portion according to the embodiment shown in FIG. 4.

The rest of the constitution of the balloon catheter 220 is the same as in the embodiment shown in FIG. 4. The balloon catheter 220 according to this embodiment exhibits the same effect as the embodiment shown in FIG. 4. In particular, in this embodiment, compared with the embodiment shown in FIG. 4, under conditions of the same total length L and the same outer diameter D1 of the tip, the internal volume is larger and the effect of assisting the heart action is greater, so this embodiment is preferable.

Next, the present invention will be explained based on specific examples.

EXAMPLE 1

Use was made of a balloon catheter 20 having a catheter tube of a length of 495 mm, wherein the inner tube 30 was formed integrally with the inner wall of the catheter tube 24 as shown in FIG. 3(B), the dimensions and shape were $D_0=2.77$ mm, $D_1=1.32$ mm, $t_0=0.28$ mm, and $t_1=0.2$ mm, and the material comprising the catheter tube 24 and the inner tube 30 was polyurethane. The response of the expansion and contraction of the catheter tube 24 were investigated under the following conditions. The results are shown next. As the fluid flowing in the catheter tube 24, use was made of helium.

The catheter tube of the balloon catheter was bent successively three times in semicircles to a curvature of a radius of about 5 cm. In that state, drive fluid was fed into or exhausted from the balloon portion through the balloon tube. The time $T_1$ until the balloon portion expanded to its maximum extent and the time $T_D$ from its maximum expansion to its contraction to its minimum extent were investigated. The average value for five measurements and the value in the zone of 95 percent reliability are shown in Table 1.

EXAMPLE 2

The same test was performed as in Example 1 except that the test was performed with the catheter tube of the balloon catheter kept straight.

The results are shown in Table 1.

TABLE 1

| | $T_1 + T_D$ |
|---|---|
| Ex. 1 | 248 ± 2 msec |
| Ex. 2 | 244 ± 2 msec |
| Comp. Ex. 1 | 276 ± 3 msec |
| Comp. Ex. 2 | 255 ± 2 msec |

COMPARATIVE EXAMPLE 1

The response of expansion and contraction of the balloon catheter was investigated under the same conditions as in Example 1 except that the inner tube was not formed integrally with the inner wall of the catheter tube and that the inner tube was inserted in a freely moving manner in the catheter tube. The results are shown in Table 1.

COMPARATIVE EXAMPLE 2

The same test was performed as in Comparative Example 1, except that the test was performed with the balloon catheter kept straight.

The results are shown in Table 1.

Evaluation

As seen from the above (examples and comparative examples), the response of expansion and contraction in the examples according to the present invention is improved over 10 percent compared with Comparative Example 1, especially in the case of Example 1. This means that if trying to obtain the same response of expansion and contraction as in Example 1 in a structure of the conditions of Comparative Example 1, it would be necessary to change the tube diameter and other facets of the structure. For example, in the tube structure of Comparative Examples 1 and 2, to keep $D_1$, $t_0$, and $t_1$ the same dimensions as in Examples 1 and 2, $D_0$ would have to be enlarged from 2.77 mm to 2.94 mm. Naturally, it would be necessary to increase the outer diameter of the catheter along with this increase. If trying to obtain the same response characteristics as the examples in a balloon catheter of the structure of the comparative examples, the outer diameter of the catheter would have to be made thicker from the 9.0 french (Fr) to 9.5 french (Fr).

If made thicker in this way, when the catheter is allowed to stand in the artery over a relatively long period, the problems arise of securing a sufficient blood flow to portions downstream of the catheter, bleeding caused along with the insertion, etc.

EXAMPLE 3

Use was made of a balloon catheter 220 having a shape as shown in FIG. 4, tapered overall from the tip to the end of the balloon portion, with D1=16 mm, D2=12 mm, L=230 mm, and l=10 mm, comprised of a polyurethane film with a thickness of the film forming the balloon portion of 0.11 mm, and with an internal volume of 28.2 cc. The durability and effect of assisting the heart action of the balloon portion were investigated under the following conditions. The results of the test are shown below.

In the test, a tapered tube made of calcium sulfate with an inside diameter $d_1$ of the large diameter side of 20 mm, an inside diameter $d_2$ of the small diameter side of 12 mm, and a length of 230 mm was prepared. The tapered tube was filled with physiological saline solution of 37° C. The balloon portion of the balloon catheter of the present example was inserted inside this and the balloon portion was expanded and contracted 1 million times. The surface conditions of the balloon portion were then investigated.

The results are shown in Table 2.

TABLE 2

| | State of surface of balloon film |
|---|---|
| Ex. 3 | No abnormalities such as scratches due to sliding wear were observed. |
| Ex. 4 | There were slight scratches due to sliding wear. |
| Ex. 5 | There were slight scratches due to sliding wear. |
| Ex. 6 | There were some scratches due to sliding wear |
| Ex. 7 | There were some scratches due to sliding wear |
| Ex. 8 | There were some scratches due to sliding wear. The thickness of the balloon film was reduced by wear. |
| Ex. 9 | There were some scratches due to sliding wear. The thickness of the balloon film was reduced by wear. |
| Comp. Ex. 3 | There are numerous scratches due to sliding wear. Leakage of the drive gas was observed after about 800,000 operations due to wear. |

TABLE 3

| | 60 bpm | 120 bpm |
|---|---|---|
| Ex. 3 | 39.6 cm$^3$ | 39.5 cm$^3$ |
| Ex. 4 | 39.5 cm$^3$ | 39.5 cm$^3$ |
| Ex. 5 | 39.6 cm$^3$ | 39.4 cm$^3$ |
| Comp. Ex. 3 | 39.6 cm$^3$ | 39.3 cm$^3$ |

Further, the pumped out volume in the case of expansion and contraction of the balloon portion of the balloon catheter of the present example in physiological saline solution at a pulsation rate of 60 bpm and 120 bpm is shown in Table 3.

EXAMPLE 4

Use was made of the same balloon catheter as in Example 3 except that the taper was from a position about ¼ L from the tip of the balloon portion to the end, D1=16 mm, D2=12 mm, L=230, l=60 mm, and the internal volume was 33 cc, and the same test as in Example 3 was performed.

The results are shown in Table 2 and Table 3.

EXAMPLE 5

Use was made of the same balloon catheter as in Example 3 except that, as shown in FIG. 6, a level difference portion was provided about ¼ L from the tip of the balloon portion so as to shape the portion to have a smaller sectional area, D1=18 mm, D2=12 mm, L=230, l=60 mm, and the internal volume was 32.2 cc, and the same test as in Example 3 was performed.

The results are shown in Table 2 and Table 3.

EXAMPLE 6

Use was made of the same balloon catheter as in Example 3 except that the taper was from a position about ½ L from the tip of the balloon portion to the end, D1=16 mm, D2=12 mm, L=230, l=115 mm, and the internal volume was 38 cc, and the same test as in Example 3 was performed.

The results are shown in Table 2.

EXAMPLE 7

Use was made of the same balloon catheter as in Example 3 except that, as shown in FIG. 6, a level difference portion was provided about ½ L from the tip portion of the balloon portion so as to shape the portion to have a smaller sectional area, D1=16 mm, D2=12 mm, L=230, and l=115 mm, and the internal volume was 37.5 cc, and the same test as in Example 3 was performed.

The results are shown in Table 2.

EXAMPLE 8

Use was made of the same balloon catheter as in Example 3 except that the taper was from a position about ¾ L from the tip of the balloon portion to the end, D1=16 mm, D2=12 mm, L=230, l=175 mm, and the internal volume was 43 cc, and the same test as in Example 3 was performed.

The results are shown in Table 2.

EXAMPLE 9

Use was made of the same balloon catheter as in Example 3 except that, as shown in FIG. 6, a level difference portion was provided about ¾ L from the tip of the balloon portion so as to shape the portion to have a smaller sectional area, D1=16 mm, D2=12 mm, L=230, and l=175 mm, and the internal volume was 42 cc, and the same test as in Example 3 was performed.

The results are shown in Table 2.

COMPARATIVE EXAMPLE 3

Use was made of a conventional balloon catheter with an outer diameter of the balloon portion of a fixed 16 mm in the longitudinal direction, with a total length L of 230 mm, comprised of a polyurethane film with a thickness of the film forming the balloon portion of 0.11 mm, and with an internal volume of 47.6 cc. The durability and the effect of assisting the heart action of the balloon portion were investigated under the same conditions as the conditions shown for Example 3. The results of the test are shown in Table 2 and Table 3.

As seen from the above-mentioned Examples 3 to 9 and Comparative Example 3, the effect of assisting the heart action is almost the same as in the comparative example, but despite this the degree of damage is much less in Examples 3 to 9.

Note that the present invention is not limited to the above embodiments or examples and may be modified in various ways within the scope and spirit of the present invention.

For example, the inner tube 30 shown in FIGS. 1-3 is not limited in application to just measurement of the blood pressure and may be used for other applications as well.

We claim:

1. An intra-aortic balloon catheter comprising:

a balloon portion which is inserted into an aorta and which repeatedly expands and contracts so as to assist pumping action of the heart;

a catheter tube connected at one end to an end of the balloon portion, the catheter tube having a first lumen introducing a pressurized gas into and leading the pressurized gas out from said balloon portion, the catheter tube having a branch portion at an end thereof opposite to the end having the balloon portion; and an inner tube having a second lumen which communicates to a blood introduction port provided at the tip of said balloon portion and extends through said balloon portion and catheter tube in the axial direction, the catheter tube being empty except for the inner tube provided therein such that the inner tube is the only structure provided within the catheter tube, and the inner tube being empty, the inner diameter and the thickness of said catheter tube being respectively from 1.5 to 4.0 mm and from 0.05 to 0.4 mm, the inner diameter and the thickness of said inner tube being respectively from 0.1 to 1.0 mm and from 0.05 to 0.4 mm, the first lumen of said catheter tube having a larger cross-sectional area than that of the second lumen, said inner tube being generally concentrically positioned within said balloon portion and being continuously affixed to the inside wall of said catheter tube from the end of the balloon portion to the branch portion of the catheter tube.

2. The intra-aortic balloon catheter as set forth in claim 1, wherein said catheter tube and inner tube are comprised of a selected material of polyurethane, polyvinyl chloride and polyethylene.

3. The intra-aortic balloon catheter as set forth in claim 1, wherein the circumferential position of said inner tube affixed to said catheter tube is generally in a straight line position along said catheter tube when the catheter tube is positioned in generally a straight line.

4. The intra-aortic balloon catheter as set forth in claim 1, wherein said inner tube is formed integrally with said catheter tube by means of an extrusion method.

5. The intra-aortic balloon catheter as set forth in claim 1, wherein said balloon catheter portion has varying cross-sectional areas from a tip side to an end side, the end side of the balloon portion being connected to the catheter tube and the cross-sectional area of the balloon portion gradually becomes smaller toward the end side from the tip side.

6. The intra-aortic balloon catheter as set forth in claim 1, wherein said balloon portion has a tip side and an end side, the end side being connected to the catheter tube, the balloon portion having cross-sectional areas of the tip side and the end side of the balloon portion which differ, the balloon portion having a step portion which is a boundary portion between the tip side and the end side, the length of the tip side of the balloon portion being more than about ¼ of a total length of the balloon portion, and the cross-sectional area of the balloon portion being smaller at the end side than the tip side.

7. The intra-aortic balloon catheter as set forth in claim 1, wherein the balloon portion has an outer diameter of 12 to 20 mm and a total length of 100 to 450 mm.

8. The intra-aortic balloon catheter as set forth in claim 1, wherein the balloon portion is made of a flexible material.

9. The intra-aortic balloon catheter as set forth in claim 1, wherein:

said balloon portion has a tip side and an end side, the balloon portion having cross-sectional areas of the tip side and the end side which differ and the cross-sectional area gradually becoming smaller toward the end side from the tip side of the balloon portion.

10. The intra-aortic balloon catheter as set forth in claim 1, wherein said inner tube is one of adhered and heat-bonded with the inside wall of said catheter tube.

11. The intra-aortic balloon catheter as set forth in claim 10, wherein said catheter tube and inner tube are comprised of a selected material of polyurethane, polyvinyl chloride and polyethylene.

12. The intra-aortic balloon catheter as set forth in claim 10, wherein the circumferential position of said inner tube affixed to said catheter tube is generally in a straight line position along said catheter tube when the catheter tube is positioned in generally a straight line.

13. The intra-aortic balloon catheter as set forth in claim 10, wherein said balloon catheter portion has varying cross-sectional areas from a tip side to an end side, the end side of the balloon portion being connected to the catheter tube and the cross-sectional area of the balloon portion gradually becomes smaller toward the end side from the tip side.

14. The intra-aortic balloon catheter as set forth in claim 10, wherein said balloon portion has a tip side and an end side, the end side being connected to the catheter tube, the balloon portion having cross-sectional areas of the tip side and the end side of the balloon portion which differ, the balloon portion having a step portion which is a boundary portion between the tip side and the end side, the length of the tip side of the balloon portion being more than about ¼ of a total length of the balloon portion, and the cross-sectional area of the balloon portion being smaller at the end side than the tip side.

15. The intra-aortic balloon catheter as set forth in claim 10, wherein the balloon portion has an outer diameter of 12 to 20 mm and a total length of 100 to 450 mm.

16. The intra-aortic balloon catheter as set forth in claim 10, wherein the balloon portion is made of a flexible material.

17. An intra-aortic balloon catheter comprising:

a balloon portion which is inserted into an aorta and which repeatedly expands and contracts so as to assist pumping action of the heart, the balloon portion having a tip and an end with a cross section of the balloon portion at the end being less than a cross section of the balloon of the tip such that a cross section of the balloon portion is non-uniform;

a catheter tube connected at one end to the end of the balloon portion, the catheter tube having a first lumen introducing a pressurized gas into and leading the pressurized gas out from said balloon portion, the catheter tube having a branch portion at an end thereof opposite to the end having the balloon portion; and an inner tube having a second lumen which communicates to a blood introduction port provided at the tip of said balloon portion and extends through said balloon portion and catheter tube in the axial direction, the catheter tube being empty except for the inner tube provided therein such that the inner tube is the only structure provided within the catheter tube, and the inner tube being empty, the inner diameter and the thickness of said catheter tube being respectively from 1.5 to 4.0 mm and from 0.05 to 0.4 mm, the inner diameter and the thickness of said inner tube being respectively from 0.1 to 1.0 mm and from 0.05 to 0.4 mm, the first lumen of said catheter tube having a larger cross-sectional area than that of the second lumen, said inner tube being positioned substantially in a concentric manner within said balloon portion and being continuously affixed to the inside wall of said catheter tube from the end of the balloon portion to the branch portion of the catheter tube.

18. An intra-aortic balloon catheter comprising:

a balloon portion which is inserted into an aorta and which repeatedly expands and contracts so as to assist pumping action of the heart, said balloon portion having a tip side and an end side, the balloon portion having cross-sectional areas of the tip side and the end side of the balloon portion which differ, the balloon portion having a step portion which is a boundary portion between the tip side and the end side, the length of the tip side of the balloon portion being more than about ¼ of a total length of the balloon portion, and the cross-sectional area of the balloon portion being smaller at the end side than the tip side;

a catheter tube connected to the end side of the balloon portion, said catheter tube introducing a pressurized gas into and leading the pressurized gas out from said balloon portion; and an inner tube which communicates with a blood introduction port provided at a tip of said balloon portion and extending through said balloon portion and catheter tube in the axial direction, said catheter tube being empty except for the inner tube provided therein such that the inner tube is the only structure provided within the catheter tube, and the inner tube being empty.

* * * * *